(12) United States Patent
Mauclaire et al.

(10) Patent No.: US 6,180,083 B1
(45) Date of Patent: Jan. 30, 2001

(54) TROPANE DERIVATIVES USEABLE IN PARTICULAR FOR IN VIVO DETECTION OF DOPAMINE TRANSPORTERS

(75) Inventors: Laurent Mauclaire, Paris; Patrick Emond, Parçay-Meslay; Denis Guilloteau, Fondettes; Jean-Claude Besnard, Quai de la Loire; Yves Frangin, Hommes, all of (FR)

(73) Assignee: CIS bio International, Saclay (FR)

( * ) Notice: Under 35 U.S.C. 154(b), the term of this patent shall be extended for 0 days.

(21) Appl. No.: 09/180,281

(22) PCT Filed: May 7, 1997

(86) PCT No.: PCT/FR97/00825

§ 371 Date: Nov. 10, 1998

§ 102(e) Date: Nov. 10, 1998

(87) PCT Pub. No.: WO97/43285

PCT Pub. Date: Nov. 20, 1997

(30) Foreign Application Priority Data

May 10, 1996 (FR) .................................... 96 05839

(51) Int. Cl.[7] .............................. A61K 51/00; C07F 7/22; C07D 451/02
(52) U.S. Cl. ............................ 424/1.85; 514/186; 546/10; 546/132
(58) Field of Search ..................... 546/10, 132; 514/186; 424/1.85

(56) References Cited

U.S. PATENT DOCUMENTS 5,493,026 * 2/1996 Elmaieh et al. .................... 546/132
5,853,696 * 12/1998 Elmaieh et al. .................... 424/1.85

* cited by examiner

Primary Examiner—Alan L. Rotman
(74) Attorney, Agent, or Firm—Oblon, Spivak, McClelland, Maier & Neustadt, P.C.

(57) ABSTRACT

The present invention relates to tropane derivatives having particular use for the in vivo detection of dopamine transporters.

These derivatives meet the formula

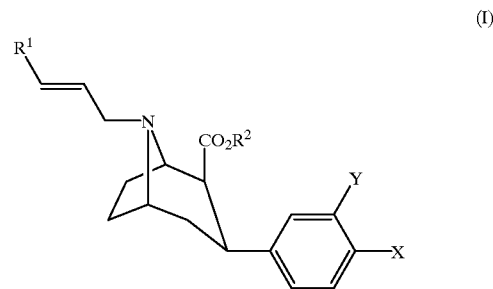

(I)

in which $R^1$ is I or Sn $(R^3)3$, $R^2$ is for example the methyl group, and X and Y are various substituents.

The derivatives with X=$CH_3$ and Y=H show strong specificity for the dopamine transporter compared with the serotonin transporter (74% inhibition when the transporter is previously saturated with GBR 12909).

36 Claims, 3 Drawing Sheets

TROPANE DERIVATIVES USEABLE IN PARTICULAR FOR IN VIVO DETECTION OF DOPAMINE TRANSPORTERS

TECHNICAL FIELD

The present invention relates to tropane derivatives which may be radioiodinated and used as iodinated radioligands for SPECT visualization (Single Photon Emission Computed Tomography) of dopamine transporters at the level of the central nervous system.

Dopamine is a neurotransmitter which is synthetized at the presynaptic neurone where it is stored. When the neurone is stimulated, dopamine is released in the synaptic gap where it diffuses. One part interacts with the receptors of the postsynaptic neurone. This interaction produces intracellular biochemical reactions which, among others, lead to propagating the nerve signal. The major part is received by the presynaptic neurone via a transporter. Inhibition of dopamine transport, by cocaine derivatives in particular, leads to an increase in dopamine level at the postsynaptic terminal of the neurone. Anomalies in dopaminergic neurotransmission are involved in neurodegenerative and psychiatric disorders such as Parkinson's and Alzheimer's disease and schizophrenia. Given the important part played by the dopamine transporter in regulating neurotransmission, the development of radioligands emitting gamma rays able to fix themselves onto the dopamine transporter with strong affinity and selectivity is necessary for visualizing this transporter for the purpose of early diagnosis of these diseases and the assessment of :

density changes in dopamine transporters over the course of the disease, and follow-up of patient treatment

STATE OF THE PRIOR ART

For this purpose, several types of ligands have been studied, such as the derivatives of GBR having the formula:

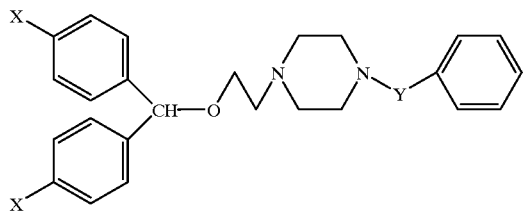

As an example of such derivatives, the following compounds can be cited which meet the above formula :

GBR 12935:X=X=H; Y=—(CH$_2$)$_3$— Kd=5.5 nM (Andersen 1987)

GBR 12783:X=X'H: Y=—CH$_2$—CH=CH— Kd=1.6 nM (Bonnet and Constantin 1986)

These types of compounds have very good in vitro affinity for the dopamine transporter. Nonetheless, in vitro competition studies with an Nonetheless, in vitro competition studies with an iodinated analogue of GBR 12783 (Foulon 1992) have shown a substantial loss in the affinity for the dopamine transporter. Also, brain biodistribution studies in rats have shown considerable non-specific fixation.

More recently, the use of iodinated analogues of cocaine has been suggested which all have the basic structure of tropane, shown below:

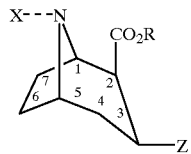

in which X, R and Z may be various substituents.

Compounds of this type are described in documents WO-A-92/02260[1], WO-A-93/09814[2], WO-A-93/18033[3], WO-A-94/04146[4], WO-A-95/11901[5], J. of Med. Chem., 1992, Vol 35, n°6, pages 969–981[6], J. Med. Chem., 1994, 37, pages 1535–1542[7], J. Med. Chem., 1995, 38, pages 379–388(8) and J. Med. Chem., 1996, 39, pages 543–548[9].

Among these tropane derivatives, a distinction can be made between a first family of compounds in which X of the above formula represents CH$_3$ and Z represents a phenyl group which may or may not be substituted, and a second family of compounds in which the may be substituted by an iodine atom and Z represents a substituted phenyl group.

Among these derivatives, those of the first family in which Z represents a phenyl group substituted by an iodine atom, have undergone particular development, for example compound RTI 55 or β-CIT described in WO-A-92/02260 [1]. However, this compound has the disadvantage of not having sufficient selectivity for dopamine transporters since it also fixes itself to serotonin transporters. Therefore, to visualize the dopamine transporter system, it is necessary to wait sufficient time until the non-specific fixation of this derivative on the serotonin transporters is eliminated .

The derivatives of the second family such as iodoaltropane (X=iodopropenyl, Z=parafluorophenyl) described in WO-A-95/11901[5] and in J. Nucl. Med., 1996, 37, pages 1197–1202[10], and [$^{125}$I] IPT (X=iodopropenyl, Z=p-chlorophenyl) described in document J. Med. Chem. 1994, 37, pages 1535–1542[7] and Synapse, 1995, 20, pages 316–324[11] show affinity and specificity for dopamine transporters. However, it would be of advantage to improve this affinity, this specificity and the kinetic properties of compounds of this type so as to make available more efficient radioligands with which visualization of the dopamine transporter systems can be obtained more quickly.

DISCLOSURE OF THE INVENTION

The object of the present invention is precisely new derivatives of tropane which have better properties than known compounds, in respect of fixation kinetics in the brain, affinity for dopamine transporters and specificity for these transporters compared with those for serotonin. Also, these new derivatives may be used to diagnose diseases such as Parkinson's disease.

Therefore the object of the invention is a compound with the formula:

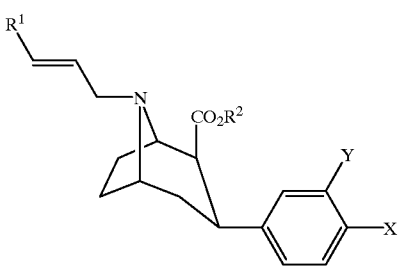

in which:
- $R^1$ represents I, a radioactive isotope of I or a group with the formula Sn $(R^3)3$ in which $R^3$ is an alkyl group;
- $R^2$ represents H ; an alkyl group in $C_1$ to $C_6$; a phenyl group; a phenyl group substituted by a halogen atom, a methyl group or a methoxy group; a phenalkyl or phenylalkenyl group whose alkyl or alkenyl group comprises 1 to 6 carbon atoms and whose phenyl group may be substituted by a halogen atom; a cycloalkyl group in $C_3$ to $C_8$ or an alkynyl group;
- X represents H, I, F, Cl, Br, —$CH_3$, —$OCH_3$, —$C_2H_5$, —$CF_3$, —OH, —$NH_2$, —$NO_2$, —CN, —NCS, $N_3$, —$NHCOCH_3$ or —$OCOCH_3$; and
- Y represents a hydrogen, chlorine, iodine or bromine atom, or the methyl group, provided that X does not represent F or Cl when Y represents H.

This compound is therefore a derivative of tropane in which the labeller (radioactive isotope of iodine) is fixed via a propenyl group onto the nitrogen atom of the basic tropane structure, the tropane being substituted in addition by a non-substituted phenyl group or substituted by one or two substituents.

Preferably, in formula (I) given above, $R^2$ represents an alkyl group, in particular the methyl group.

Again preferably, in formula (I) given above, the phenyl group is non-substituted or substituted in para position by $CH_3$, I, $CF_3$, $C_2H_5$ or $NH_2$.

According to one variant of embodiment of the invention, the phenyl group comprises two substituents of which one is a halogen. For example X represents Cl or F and Y represents $CH_3$, or X represents $NH_2$ and Y represents Br or I.

When $R^1$ represents a radioactive iodine atom, the latter may be $^{125}$I, $^{123}$I or $^{131}$I as these isotopes are suitable for in vivo visualization of dopamine transporters at SPECT (Single Photon Emission Computed Tomography) owing to their relatively short radioactive period.

For this study, the compounds of the invention may be used in the form of pure isomers or a mixture of isomers. However, better results are obtained when a compound with $R^1$ in position E is used.

$R^1$ may also represent the group Sn $(R^3)$ with $R^3$ being an alkyl group preferably having 1 to 8 carbon atoms, for example the n-butyl group. Such derivatives are intermediate products of interest in the preparation of iodinated and radioiodinated derivatives.

The compounds of the invention may be prepared by conventional processes such as that described by Goodman et al in J. Med. Chem., 1994, 37, pages 1535–1542. This synthesis corresponds to the reaction diagram illustrated in FIG. 1.

Owing to their specificity and their affinity for dopamine transporters, the compounds of the invention may be used in pharmaceutical and radiopharmaceutical compositions. Such compositions comprise the compound of formula (I) described above in which $R^1$ represents I or a radioactive isotope of I, and $R^2$, X and Y have the signification given above, and a pharmaceutically acceptable vehicle. In radiopharmaceutical compositions, $R^1$ represents a radioactive isotope of I.

These compositions may, in particular, be in the form of injectable solutions comprising from $10^{-5}$ to $10^{-3}$ mg/l of compound. For the in vivo visualization of dopamine transporters in the central nervous system, an appropriate quantity of solution may be injected into the patient to be examined, and the patient may be examined under a SPECT scanner 0.5 to 2 hours after the injection. The dose injected may be between 0.005 and 0.5 $\mu$g per kg body weight, i.e. a radioactivity of 35 MBq to 370 MBq per injection.

Other characteristics and advantages of the invention will be better understood on reading the following examples with reference to the appended drawings.

SHORT DESCRIPTION OF THE DRAWINGS

DETAILED DESCRIPTION OF EMBODIMENTS

Figure 1:
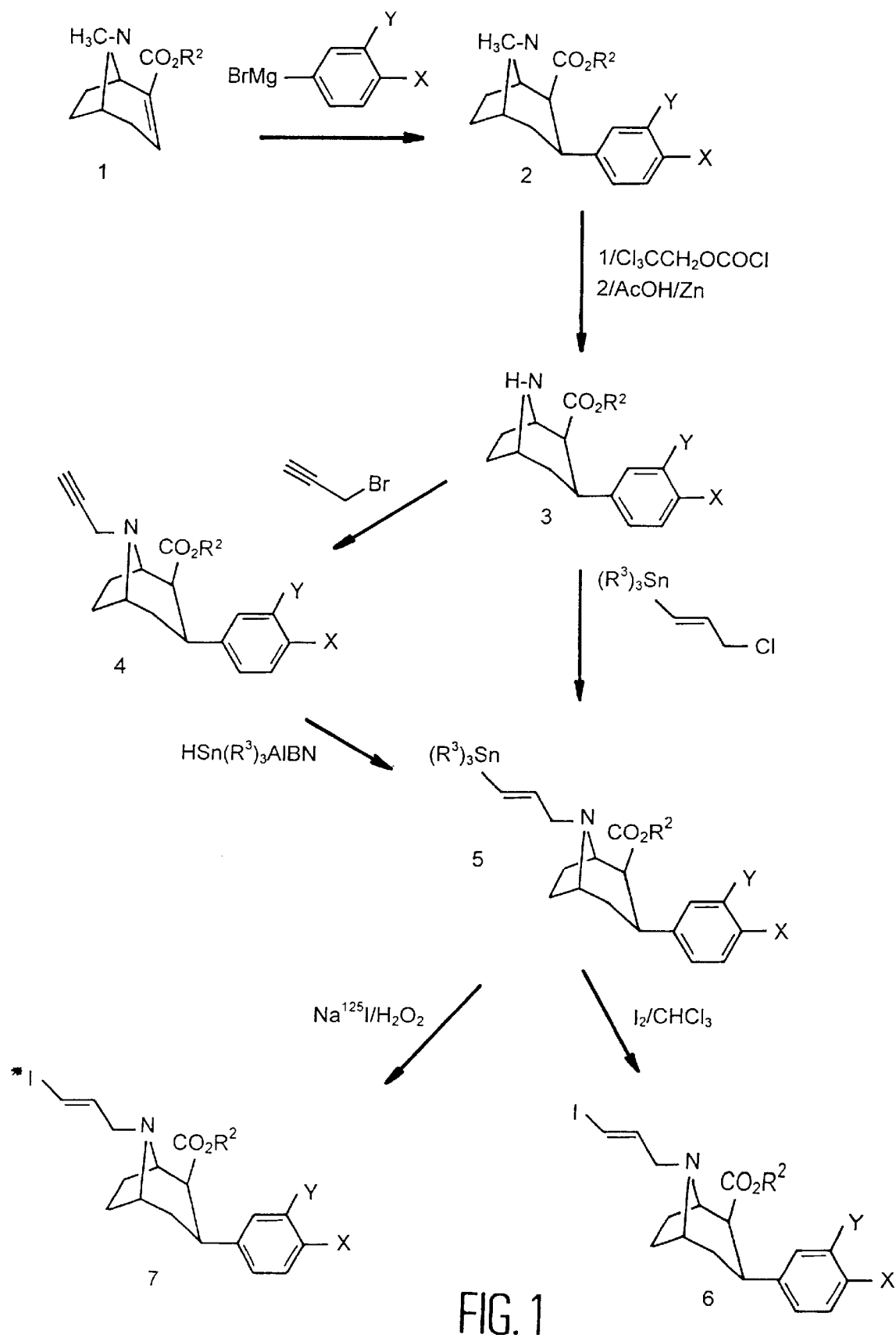
FIG. 1 is a synthesis reaction diagram of the compounds of the invention.

FIG. 1 shows the possible synthesis diagrams of the compounds of the invention.

In this synthesis diagram, an ester of anhydroecgonine 1 is used, that is caused to react with the arylmagnesium bromide corresponding to the phenyl group of the compound of formula (I) to be prepared. In this way compound 2 is obtained which is converted into compound 3 by reaction with trichloroethylchloroformate and treatment with a mixture of acetic acid and zinc chips.

Compound 3 is then converted into compound 5 either directly by reaction with 3-chloro-1-tri-alkylstannyl-prop-1-ene, or in two stages by reaction with 1-bromo-2-propyne to obtain compound 4 which is converted into compound 5 with trialkylstannyl hydride. Compound 5 may be converted into non-radioactive compound 6 by reaction with iodine in the presence of chloroform, or into a radioactive compound by reaction with sodium iodide Na$^{125}$I in the presence of an oxidizing agent such as hydrogen peroxide.

EXAMPLE 1

Preparation of 2-β-carbomethoxy-3β-paramethylphenyl)-8-(3-[$^{125}$I]iodoprop-2E-enyl)nortropane (7)

This compound corresponds to compound 7 of FIG. 1 where $R^2$=CH$_3$, Y=H and X=CH$_3$.

For this preparation, the operating mode in FIG. 1 is followed.

a) Preparation of 2β-carbomethoxy-3β-methylphenyl) tropane (2)

The anhydroecgonine methyl ester 1 (1eq.) is dissolved in 25 ml of anhydrous ether and then added to 5 eq. of (methylphenyl) magnesium bromide at −40° C. After 3 hours of mechanical stirring, the mixture is cooled to −78° C. and treated drop by drop with a solution of 5 ml of trifluoroacetic acid diluted in 25 ml of anhydrous ether. After one hour's stirring, the mixture is brought to 0° C. and then treated with 70 ml of water and 26 ml of concentrated HCl. The aqueous phase is then treated with $NH_4OH$ and extracted with ether (3×40 ml). The different organic phases are collected, washed in brine, dried on $Na_2SO_4$ and evaporated to produce compound 2 with a yield of 30%.

The NMR characteristics (200 MHz, $CDCl_3$) are given in table I.

b) Preparation of 2β-carbomethoxy-3β(p-methyl phenyl) nortropane (3)

A mixture of compound 2 obtained previously (1 eq.) and trichloroethylchloroformate (5.5 eq.) is brought to 120° C. and shaken for 75 min. After return to ambient temperature, the trichloroethylchloroformate in excess is distilled under reduced pressure. The raw carbamate thus obtained is dissolved in 15 ml (1 eq.) of acetic acid, then treated with zinc chips (25 eq.). The mixture is shaken at ambient temperature for 16 hours, treated with -*/ of the celite and filtered. The filtrate is extracted with chloroform, washed in brine, dried on $Na_2SO_4$ and evaporated. This reaction, after purificaiton by flash chromatography (silica, $Et_2O$, $Et_3N$ 75/25) leads to compound 3 with yield of 70%.

c) Preparation of 2β-carbomethoxy-3β(p-methylphenyl)-8-(3-tributylstannylprop-2E-enyl) nor-tropane (5).

Compound 3 obtained previously (1 eq.) and the 3-chloro-1E-(tri-n-butylstannyl)prop-1-ene (1 eq.) are dissolved in 2 ml/eq of absolute ethanol containing a catalytic quantity of KI. The mixture is shaken and heated to 70° C. for 16 hours. After return to ambient temperature, the mixture is treated with $NaHCO_3$ and extracted with ether. The organic phase is washed in brine, dried on $Na_2SO_4$ and evaporated to give compound 5. Each product is purified on a silica preparation plate using petroleum ether/AcOEt 9/1 as elution phase.

NMR characteristics (200 MHz, $CDCl_3$):
For this product the following are observed:
a doublet at 5.96 ppm ; J3=19 Hz, i=1H
a doublet of a doublet split at 5.80 ppm, i=H d) Preparation of 2β-carbomethoxy-3β-(p-methylphenyl)-8-(3-[$^{125}$I] iodoprop-2E-enyl)nortropane (7).

To a solution containing 50 mg of compound 5 obtained at c), 50 µl of 0.1 N HCl and 50 µl of 3% w/v $H_2O_2$ are added 5 µl of $Na^{125}I$ (37 MBq/ml, 1 mCi/ml). The reaction is left at ambient temperature for 15 minutes then stopped with the addition of 100 µl of a sodium bisulphite solution (300 mg/ml). The reaction medium is then made alkaline with a solution of $NaHCO_3$ (500 mg/ml) and extracted with AcOEt (3×1 ml). The organic phase is evaporated under a stream of nitrogen and the raw product is purified by high performance liquid chromatography (HPLC) under the following operating conditions:
Column C18; flow rate 1 ml/min; mobile phase $MeOH/H_2O/Et_3N(75/25/0.2)$; Elution time=13 min.

The fraction containing the desired product is collected, concentrated on Sep Pak C18, then extracted with 2×1 ml of $CHCl_3$. The chloroform is evaporated under a stream of nitrogen. The residue is recovered with an aqueous solution.

EXAMPLE 2

Preparation of 2β-carbomethoxy-3β-(p-methylphenyl)-8(3 iodoprop-2E-enyl)nortropane (6).

In this example the same operating mode as in example 1 is followed, to prepare compound 5 of stage c) of example 1.

This compound 5 is treated with a solution of $I_2$ (1 M) in $CHCl_3$ at 0° C. until a yellow colour appears. The mixture is then washed in 10% $NaHCO_3$ in water, dried on $Na_2SO_4$ and evaporated. The raw product is purified on a silica preparation plate using petroleum ether/AcOEt/9/1 as elution phase.

NMR characteristics (200 MHz, $CDCl_3$):
For this product the following are observed:
one doublet at 6.23 ppm ; J3=14.3, i=1H ; one body at 6.50 ppm, i=1H.

EXAMPLES 3 and 4

Preparation of $^{125}$I labelled compounds

In these examples, the compounds meeting the formula given in table 2 with the X and Y also shown in this table, are prepared following the same operating mode as in example 1.

The NMR characteristics (200 MHz, $CDCl_3$) of the intermediate compounds and the yields of the reactions are given in table 1.

For the intermediate products obtained stage c), the following are observed:
one doublet at 5.96 ppm;
J3=19 Hz
i=1H ; one doublet of a doublet split at 5.80 ppm, i=1H.

EXAMPLES 5 to 13

In these examples, the compounds meeting the formulae given in table 2 with X and Y having the signification given in this table, are prepared following the same operating mode as in example 1.

The desired compounds are obtained with satisfactory yields.

In table 2 are also given two compounds of the prior art; IPT described in documents 7 and 11, and the iodoaltropane described in documents 5 and 10.

EXAMPLE 14

In this example, in vivo tests in the rat are used to study the affinity and specificity of the compound of example 1, hereinafter called PE21, for the dopamine transporter.

For this purpose 3 batches of male Wistar rats are used using 6 rats per batch. Batch number 1 is first given an intravenous injection of GBR 12909 (specific inhibitor of the dopamine transporter produced by RBI Bioblock) at a dose of 5 mg/kg, and 30 minutes later an injection of the compound of example 1 is given by intravenous route, at a dose of $8.10^{-6}$ mg/kg.

Batch number 2 first receives an injection of paroxetine (specific inhibitor of the serotonin transporter made by Beecham laboratories) at a dose of 5 mg/kg, and 30 minutes later an injection of the compound of example 1 is given under the same conditions as for batch number 1.

Batch number 3, or the reference batch, only receives an intravenous injection of the compound of example 1.

2 hours later, the animals are sacrificed and the doses of radioactivity in the cerebellum, striatum and frontal cortex tissues are determined.

Figure 2:
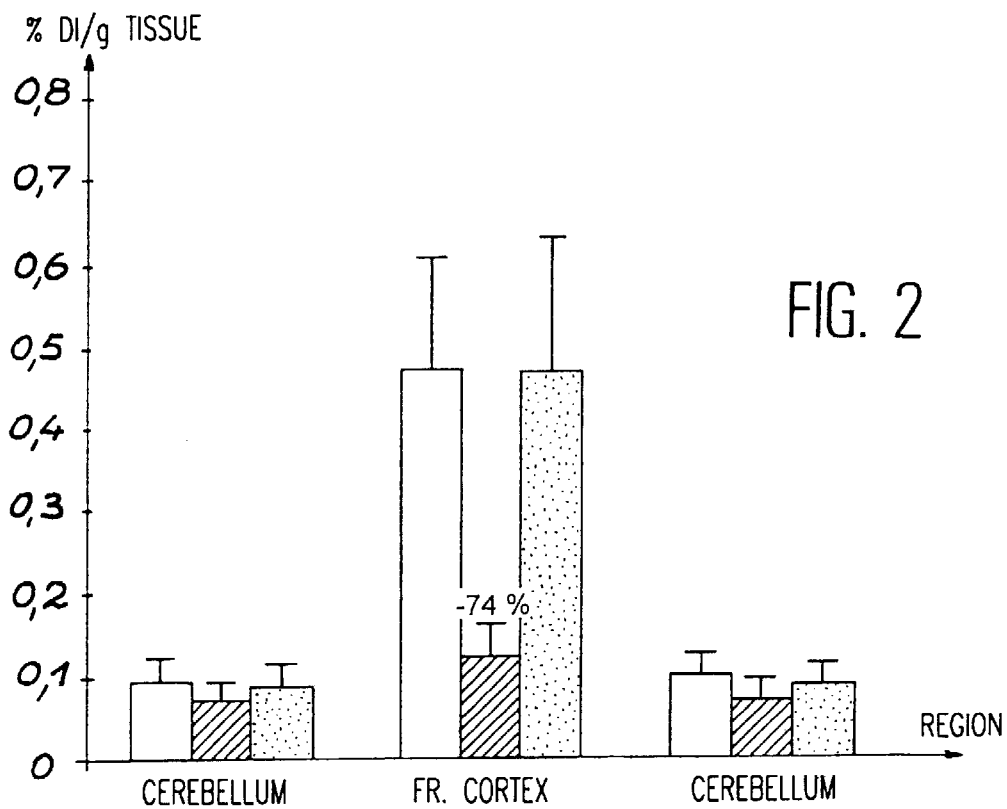
FIG. 2 is a diagram illustrating the fixation of a derivative of the invention on the cerebellum, striatum and frontal cortex expressed as a percentage of the dose injected per gram of tissue.

The results obtained are given in FIG. 2 and are expressed as a % of the dose injected per gram of tissue.

In this figure, the columns in white relate to batch number 3 (reference), the shaded columns relate to batch number 1 which received GBR 12909 and the dotted columns relate to batch number 2 which received paroxetine.

In this figure it can be seen that the fixation in the striatum of the compound of example 1 in accordance with the invention is prevented by 74% through a preinjection of GBR 12909. The compound of the invention is therefore specific to the dopamine transporter since a saturation of this transporter with a specific inhibitor (GBR 12909) prevents its fixation.

COMPARATIVE EXAMPLE 1

In this example, the same operating mode as in example 14 is followed to conduct the same in vivo brain biodistribution study in the rat, but using the compound of the prior art β-CIT (3b-4-iodo[$^{125}$I]phenyl)-tropan-2β-carboxylic acid methyl ester) instead of the compound of example 1.

Figure 3:
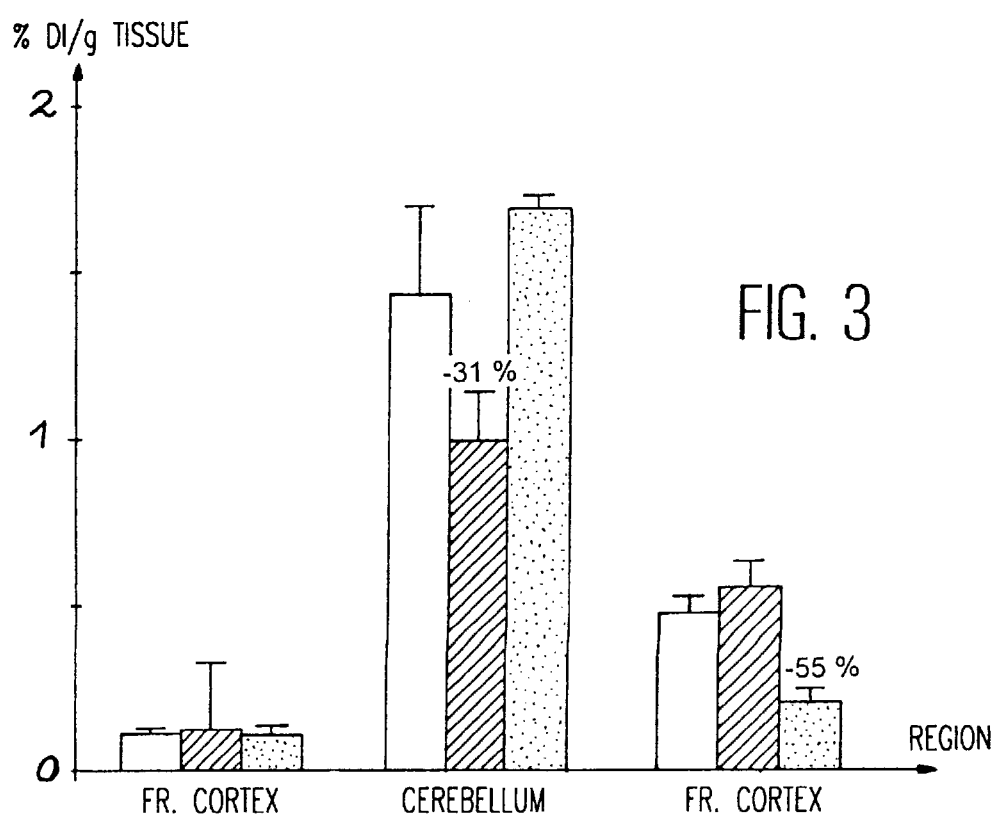
FIG. 3 is a diagram illustrating the fixation of a compound of the prior art (β-CIT) on the cerebellum, striatum and frontal cortex under the same conditions as in FIG. 2, also being expressed as a percentage of the dose injected per gram of tissue.

The results obtained are shown in FIG. 3 using the same symbols.

In this figure, it can be seen that the fixation of the compound of the prior art in the striatum is only inhibited by 31%. This residual fixation of [$^{125}$I]-βCIT is therefore due to binding at sites that are not dopamine transporters, which is much greater than that obtained with the compound of the invention.

Also, in the frontal cortex which is rich in serotonin transporter sites, the fixation of the compound of the prior art [$^{125}$I]-βCIT is much higher than that of the compound of the invention. Also, it is inhibited by 55% through a preinjection of paroxetine.

The compound of the invention is therefore seen to have very strong specificity for the dopamine transporter compared with the serotonin transporter, which is not the case with β-CIT which binds to both these transporters.

Also, the compound of the invention has a very strong specificity for the dopamine transporter in the striatum at early times (2 hours).

The non-specific fixation in the striatum determined after saturation with GBR 12909 is approximately 25%, whereas it is in the region of 70% for β-CIT.

EXAMPLE 15

In this example, a biodistribution study in the rat is also conducted for the compound of example 1 following the same operating mode as in example 14, but sacrificing the animals at ½ hour, 1 hour or 4 hours after injection.

The results obtained are given in table 3. In this table, the results obtained in example 14 are also given.

These results show that the product accumulates in preferential manner in the striatum and that the maximum striatum over frontal cortex or cerebellum ratio is obtained for early times (between 0.5 and 1 h after injection).

EXAMPLE 16

In this example, in vitro studies are conducted on brain membrane preparations.

These studies are competition studies between [$^3$H]-GBR 12935 (dopamine transporter), [$^3$H]-paroxetine (serotonin transporter), [$^3$H]-nisoxetine (noradrenaline transporter) and the iodinated derivative of example 1 (PE21).

The inhibition constants Ki (nM) obtained with the compound of the invention PE21 in competition with the different ligands are given in table 4.

By way of comparison, table 4 also shows the results obtained with the β-CIT ligand, i.e. 2β-carbomethoxy-3β-(4' iodophenyl)-tropane, and the results given in table I of document 10: J. Nucl. Med., 1996, 37, pages 1197–1202 for tests of the same type conducted with β-CIT and iodoaltropane described in WO-A-95/11901.

On reading this table it is noticed that the compound of the invention PE21 has better specificity (Ki(5-HT): Ki (DA)= 29.4) for dopamine transporters than iodoaltropane (Ki(5-HT): Ki (DA)=25).

Also, if the affinity of these two compounds is compared with that of β-CIT it will be seen that the Ki ratio: DA (iodoaltropane)/DA (β-CIT) is 6 whereas the Ki ratio: DA (PE21)/DA(β-CIT) is 0.63, which shows the better affinity (10 times more affinity) of compound PE21 of the invention.

Also compound PE21 of the invention has better specificity and better affinity than compound IPI of the prior art (document 11).

In document 11 the affinity constant of IPT for dopamine transporters is seen to be Kd=0.25±0.02 nM (table 1) and that this affinity constant for serotonin transporters is Kd=1.2±0.02 nM (page 320). Therefore a specificity Kd(5-HT)/Kd(DA) of approximately 5 is obtained.

With compound PE21 of the invention, this specificity is distinctly greater since Ki(5-HT)/Ki(DA) is 29.4 as can be seen in table 4.

Therefore, PE21 is 5 times more specific than IPT.

The affinity of compound [$^{125}$I]PE21 for dopamine transporters was also determined in vitro, and the following value was obtained:

Kd=0.09±0.01 n.

By way of comparison, the affinity of compound IPT for dopamine transporters described in document 11 corresponds to:

Kd=0.25±0.02 nM.

It emerges from these results therefore that PE21 has an affinity that is 2.5 times higher than the near compound IPT.

These results show the superiority of compound PE21 of the invention in relation to the nearest compounds of the prior art. Yet it was unforeseeable that replacement of a Cl or F atom by a methyl group could lead to such biological superiority.

EXAMPLE 17

In this example, a kinetics study in vivo is made on the brain distribution of the compound of example 1 in primates (Cynomologus female macaque, 2 kg, anaesthetized with ketamine, with data acquisition made every 12 minutes on CERASPECT).

Figure 4:
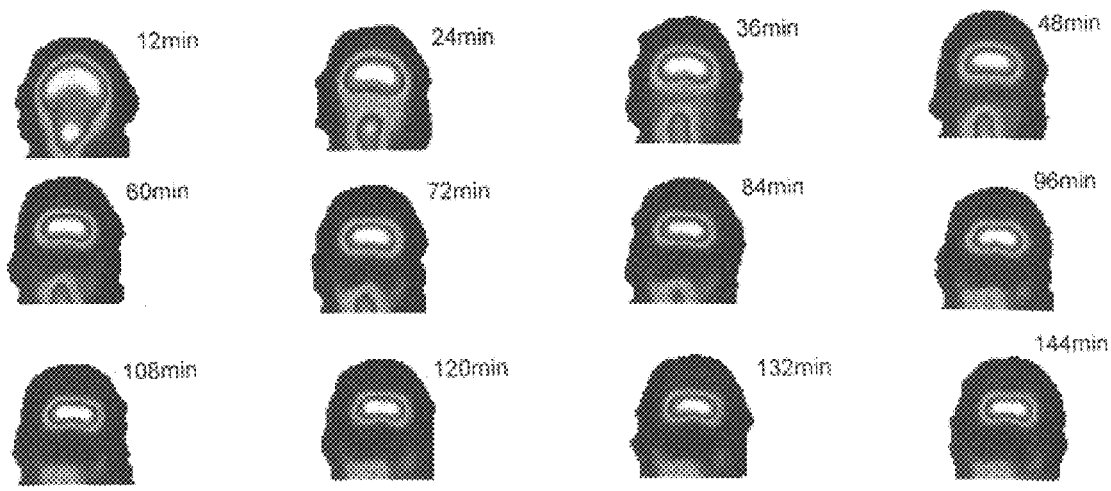
FIG. 4 illustrates the results obtained for the visualization of dopamine transporters in primates in relation to time.

The results of this study are given in FIG. 4.

In this figure it can be seen that the compound of example 1 binds itself in specific manner at the central grey nuclei and that an image of these structures is obtained between 1 hour and 2 hours after injection.

On the hand, the compound of the prior art β-CIT only starts producing a specific image of these structures after 20 hours.

The compound of the invention is therefore of great interest for the in vivo visualization of the dopamine transporter system.

EXAMPLE 18

In this example, the compound of example 1 PE21 was tested in the rat using a model of Parkinson's disease obtained with a unilateral lesion of the nigrostriatal pathway. For this purpose Wistar rats were unilaterally perfused in the substantia nigra with 8 μg of 6-OHDA(6-hydroxy dopamine).

Three weeks later, they were given an intravenous 3.7 MBq injection of [$^{125}$I]PE21.

Two hours afterwards, the rats were sacrificed and their brains collected. The latter were frozen and coronal sections 20 μm thick were taken which were exposed on β-max hyperfilm for six weeks.

The striatum/frontal cortex ratios were calculated after analysis of the films. On the lesion side, an average ratio of 0.86±0.10 was observed, while this ratio was 7.20±0.91 on the intact side.

These results obtained on ex vivo autoradiographs show that PE21 is suitable for the in vivo detection of specific lesions of dopaminergic cells.

TABLE I

NMR Characteristics (200 MHz, CDCl$_3$)

| Compound | Ph-CH$_3$ | N—CH$_3$ | CO$_2$CH$_3$ | H aromatics |
|---|---|---|---|---|
| Ex. 1 stage a) yield: 30% | s, i = 3, 2, 11 | s, i = 3, 2, 17 | s, i = 3, 3, 23 | 2d, 1 = 4, 6.93–7.06 |
| Ex. 3 stage a) tield: 59% | | s, i = 3, 2, 15 | s, i = 3, 3, 41 | m, i = 5, 7, 18 |
| Ex 4 stage a) yield: 22% | | s, i = 3, 2, 14 | s, i = 3, 3, 42 | 2d, i = 4.6, 94 and 7.50 |
| Ex 1 stage b) yield: 70% | s, i = 3, 2, 33 | | s, i = 3, 3, 40 | s, i = 4, 7, 11 |
| Ex 3 stage b) yield: 80% | | | s, i = 3, 3, 28 | m, i = 5, 7, 13 |
| Ex 4 stage b) yield: 54% | | | s, i = 3, 3, 27 | 2d = 6.89 and 7.13 s = 7, 14 |

TABLE 2

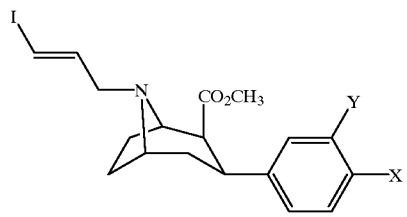

| Compound | X | Y |
|---|---|---|
| Example 1 | CH$_3$ | H |
| Example 3 | H | H |
| Example 4 | I | H |
| Example 5 | CF$_3$ | H |
| Example 6 | C$_2$H$_5$ | H |
| Example 7 | Cl | CH$_3$ |
| Example 8 | H | Cl |
| Example 9 | H | I |
| Example 10 | F | CH$_3$ |
| Example 11 | NH$_2$ | H |
| Example 12 | NH$_2$ | Br |
| Example 13 | NH$_2$ | I |
| IPT | Cl | H |
| Altropane | F | H |

TABLE 3

| Post-injection time (hours) | Cerebellum | Striatum (% injected dose/ g tissue) | Frontal cortex (% injected dose/ g tissue) |
|---|---|---|---|
| 0.5 | 0.100 ± 0.015 | 1.061 ± 0.132 | 0.124 ± 0.020 |
| 1 | 0.055 ± 0.010 | 0.537 ± 0.102 | 0.070 ± 0.016 |
| 2 | 0.038 ± 0.010 | 0.272 ± 0.084 | 0.039 ± 0.06 |
| 4 | 0.021 ± 0.002 | 0.074 ± 0.030 | 0.018 ± 0.004 |

TABLE 4

| Ligand | Affinity: Ki (nM) | | | Selectivity |
|---|---|---|---|---|
| | Dopamine (DA) | Serotonin 5-HT | Nor-adrenaline | D5-HT/ DA |
| PE21 (compound example 1) | [$^3$H]GBR 17 ± 7 | [$^3$H]paroxetine 500 ± 80 | [$^3$H]nisoxetine >100 | 29.4 |
| β-CIT | [$^3$H]GBR 27 ± 2 | [$^3$H]paroxetine 30 ± 2 | [$^3$H]nisoxetin 80 ± 28 | 1.11 |
| Iodo-altropane (document 10) | [$^3$H]Win35428 6.62 ± 0.78 | [$^3$H]citalopram 182 ± 41.8 | | 25 |
| β-CIT (document 10) | [$^3$H]WIN35428 1.08 ± 0.6 | [$^3$H]citalopram 2.53 ± 0.02 | | |

CITED REFERENCES

1: WO-A-92/02260
2: WO-A-93/09814
3: WO-A-93/18033
4: WO-A-94/04146
5: WO-A-95/11901
6: J. Med. Chem., 1992, vol 35, n°6, pages 969–981
7: J. Med. Chem., 1994, vol 37, pages 1535–1542
8: J. Med. Chem., 1995, vol 38, pages 379–388
9: J. Med. Chem., 1996, vol 39, pages 543–548
10: J. Nucl. Med., 1996, vol 37, pages 1197–1202
11: Synapse, 1995, 20, pages 316–324

What is claimed is:

1. A compound represented by the formula:

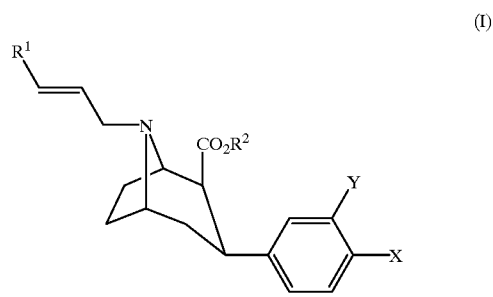

(I)

wherein
R$^1$ represents I, a radioactive isotope of I or a group with the formula Sn(R$^3$)$_3$ in which R$^3$ is an alkyl group;
R$^2$ represents H, a C$_1$ to C$_6$ alkyl group; a phenyl group; a phenyl group substituted by a halogen atom, a methyl group or a methoxy group; a phenylalkyl or phenylalkenyl group whose alkyl or alkenyl group comprises 1 to 6 carbon atoms and whose phenyl group may be substituted by a halogen atom; a $C_3$ to $C_8$ cycloalkyl group or an alkynyl group;

wherein X represents Cl or F, and Y represents $CH_3$.

2. The compound of claim 1, wherein $R^2$ is a methyl group.

3. A compound represented by the formula:

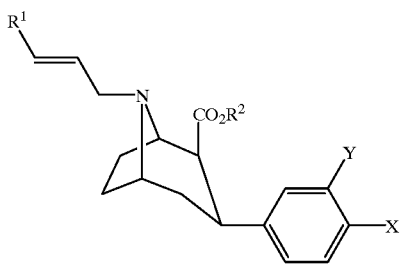

(I)

wherein $R^1$ represents I, a radioactive isotope of I or a group with the formula $Sn(R^3)_3$ in which $R^3$ is an alkyl group;

$R^2$ represents H; a $C_1$ to $C_6$ alkyl group; a phenyl group; a phenyl group substituted by a halogen atom, a methyl group or a methoxy group; a phenylalkyl or phenylalkenyl group whose alkyl or alkenyl group comprises 1 to 6 carbon atoms and whose phenyl group may be substituted by a halogen atom; a $C_3$ to $C_8$ cycloalkyl group or an alkynyl group;

wherein X represents $NH_2$ and Y represents Br or I.

4. The compound of claim 1, wherein $R^1$ represents $^{125}I$, $^{123}I$ or $^{131}I$.

5. The compound of claim 3, wherein $R^1$ represents $^{125}I$, $^{123}I$ or $^{131}I$.

6. A compound represented by the formula:

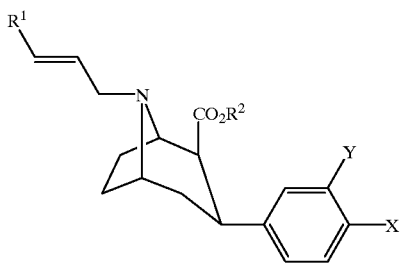

(I)

wherein $R^1$ represents $Sn(C_4H_9)_3$, $^{125}I$, $^{123}I$ or $^{131}I$, $R^2$ represents $CH_3$, X represents $CH_3$, and Y represents H.

7. The compound of claim 1, wherein $R^1$ is at position E.

8. A process for preparing a compound represented by the formula:

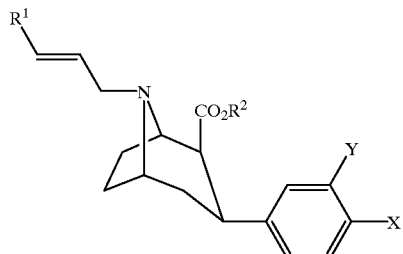

(I)

wherein $R^1$ represents I;

$R^2$ represents H; a $C_1$ to $C_6$ alkyl group; a phenyl group; a phenyl group substituted by a halogen atom, a methyl group or a methoxy group; a phenylalkyl or phenylalkenyl group whose alkyl or alkenyl group comprises 1 to 6 carbon atoms and whose phenyl group may be substituted by a halogen atom; a $C_3$ to $C_8$ cycloalkyl group or an alkynyl group;

wherein X represents Cl or F, and Y represents $CH_3$, comprising 1) reaction of an arylmagnesium bromide having the formula:

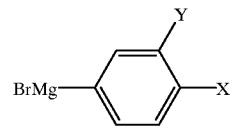

wherein X and Y are as defined above, with an ester of anhydroecgonine (1) having the formula:

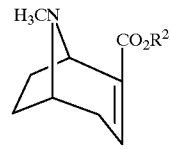

wherein $R^2$ is as defined above, to obtain a compound (2) having the formula:

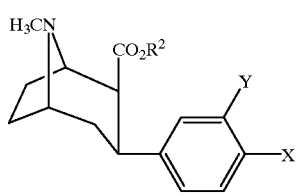

2

2) conversion of compound (2) into compound (3) having the formula:

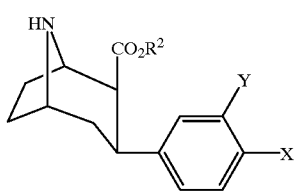

3 through reaction with trichloroethyl chloroformate and reduction with zinc and acetic acid, 3) conversion of compound (3) into compound (5) having the formula:

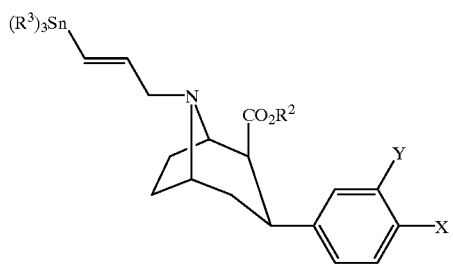

5 wherein $R^3$ is an alkyl group, and 4) reaction of compound (5) with iodine to obtain the compound of formula (I) as defined above.

9. A process for preparing a compound represented by the formula:

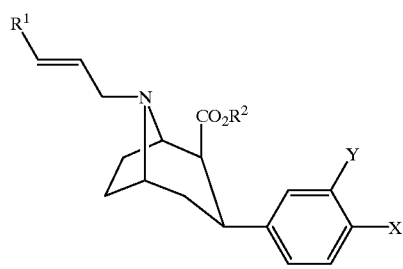

(I)

wherein $R^1$ represents a radioactive isotope of I;

$R^2$ represents H; a $C_1$ to $C_6$ alkyl group; a phenyl group; a phenyl group substituted by a halogen atom, a methyl group or a methoxy group; a phenylalkyl or phenylalkenyl group whose alkyl or alkenyl group comprises 1 to 6 carbon atoms and whose phenyl group may be substituted by a halogen atom; a $C_3$ to $C_8$ cycloalkyl group or an alkynyl group;

wherein X represents Cl or F, and Y represents $CH_3$, comprising:

1) reaction of an arylmagnesium bromide having the formula:

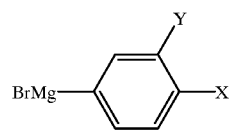

wherein X and Y are as defined above, with an ester of anhydroecgonine (1) having the formula:

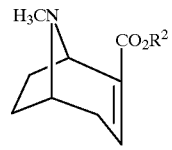

1 wherein $R^2$ is as defined above to obtain a compound (2) having the formula:

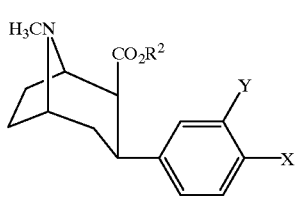

2

2) conversion of compound (2) into compound (3) having the formula:

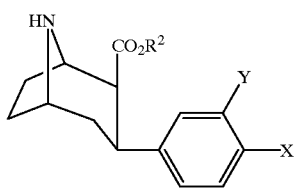

3 through reaction with trichloroethyl chloroformate and reduction with zinc and acetic acid, 3) conversion of compound 3 into compound (5) having the formula:

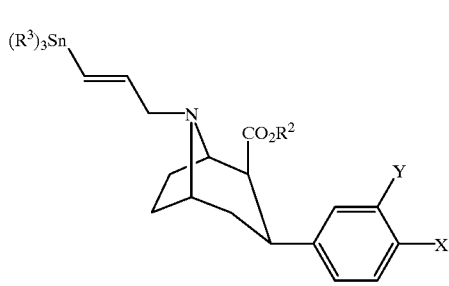

5 wherein $R^3$ is an alkyl group, and 4) reaction of compound (5) with the iodide of formula Na*I wherein *I is a radioactive isotope of iodine, in the presence of an oxidizing agent.

10. The process of claim 8, wherein in stage 3) compound (3) is converted directly into compound (5) through reaction with 3-chloro-1-trialkylstannyl-prop-1-ene.

11. The process of claim 9, wherein in stage 3) compound (3) is converted directly into compound 5 through reaction with 3-chloro-1-trialkylstannyl-prop-1-ene.

12. The process of claim 8, wherein in stage 3) firstly compound (3) is caused to react with 1-bromo-2-propyne to obtain the compound having the formula:

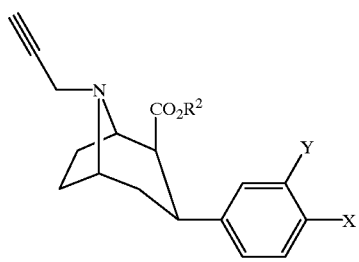

then compound (4) is caused to react with trialkylstannyl hydride to obtain compound (5).

13. The process of claim 9, wherein in stage 3) firstly compound (3) is caused to react with 1-bromo-2-propyne to obtain the compound having the formula:

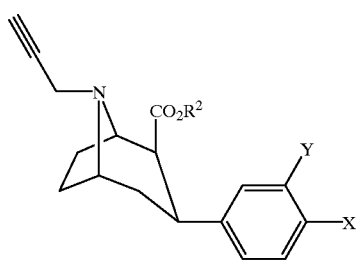

then compound (4) is caused to react with trialkylstannyl hydride to obtain compound (5).

14. A pharmaceutical composition, comprising a compound represented by the formula:

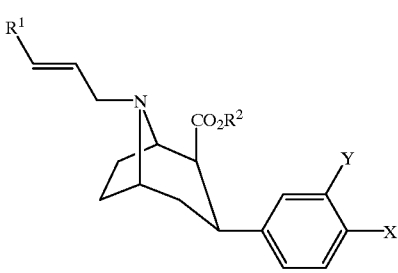

wherein $R^1$ represents $^{125}I$, $^{123}I$ or $^{131}I$, $R^2$ represents $CH_3$, X represents $CH_3$, Y represents H and $R^1$ is at the E position; and
a pharmaceutically acceptable vehicle.

15. A radiopharmaceutical composition comprising a compound represented by the formula:

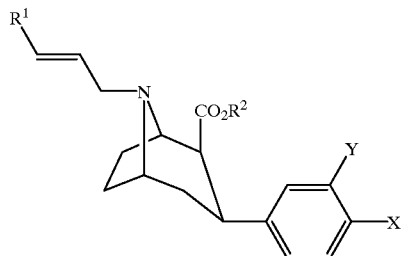

wherein $R^1$ represents $^{125}I$, $^{123}I$ or $^{131}I$, $R^2$ represents $CH_3$, X represents $CH_3$, Y represents H and $R^1$ is at the E position;
and a pharmaceutically acceptable vehicle.

16. The composition of claim 15, wherein it is in injectable solution form.

17. The composition of claim 14, wherein it is in injectable solution form.

18. The radiopharmaceutical composition of claim 15, for the visualization of dopamine transporters in the central nervous system.

19. The compound of claim 1, wherein $R^1$ represents $Sn(C_4H_9)_3$, $^{125}I$, $^{123}I$ or $^{131}I$, and $R^2$ represents $CH_3$.

20. The compound of claim 3, wherein $R^2$ is a methyl group.

21. The compound of claim 3, wherein $R^1$ represents $Sn(C_4H_9)_3$, $^{125}I$, $^{123}I$ or $^{131}I$, and $R^2$ represents $CH_3$.

22. The compound of claim 3, wherein $R^1$ is at position E.

23. The compound of claim 6, wherein $R^1$ is at position E.

24. A process for preparing a compound represented by the formula:

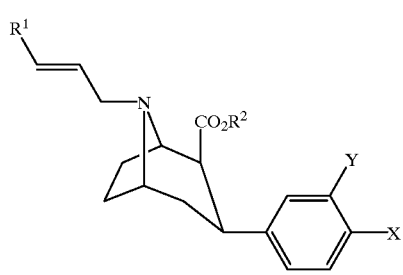

wherein
$R^1$ represents I;
$R^2$ represents H; a $C_1$ to $C_6$ alkyl group; a phenyl group; a phenyl group substituted by a halogen atom, a methyl group or a methoxy group; a phenylalkyl or phenylalkenyl group whose alkyl or alkenyl group comprises 1 to 6 carbon atoms and whose phenyl group may be substituted by a halogen atom; a $C_3$ to $C_8$ cycloalkyl group or an alkynyl group;
wherein X represents $NH_2$ and Y represents Br or I, comprising
1) reaction of an arylmagnesium bromide having the formula:

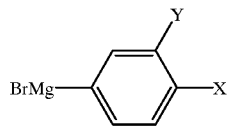

wherein X and Y are as defined above, with an ester of anhydroecgonine (1) having the formula:

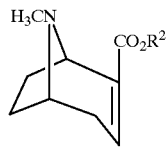

wherein $R^2$ is as defined above, to obtain a compound (2) having the formula:

2

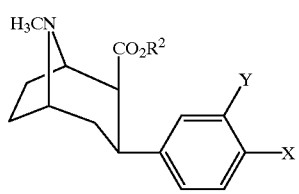

2) conversion of compound (2) into compound (3) having the formula:

3

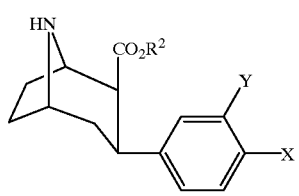

through reaction with trichloroethyl chloroformate and reduction with zinc and acetic acid, 3) conversion of compound (3) into compound (5) having the formula:

5

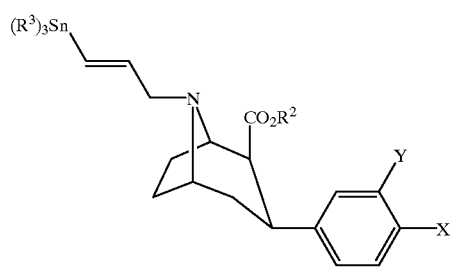

wherein $R^3$ is an alkyl group, and 4) reaction of compound (5) with iodine to obtain the compound of formula (I) as defined above.

25. A process for preparing a compound represented by the formula:

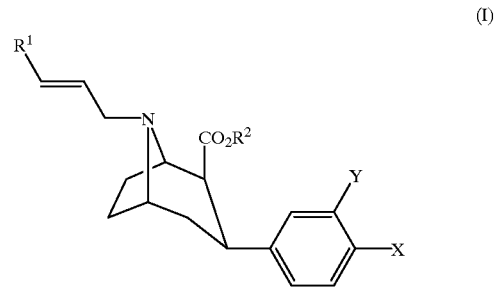

(I)

wherein $R^1$ represents a radioactive isotope of I;

$R^2$ represents H; a $C_1$ to $C_6$ alkyl group; a phenyl group; a phenyl group substituted by a halogen atom, a methyl group or a methoxy group; a phenylalkyl or phenylalkenyl group whose alkyl or alkenyl group comprises 1 to 6 carbon atoms and whose phenyl group may be substituted by a halogen atom; a $C_3$ to $C_8$ cycloalkyl group or an alkynyl group;

wherein X represents $NH_2$ and Y represents Br or I, comprising:

1) reaction of an arylmagnesium bromide having the formula:

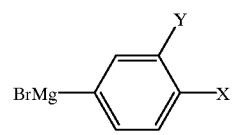

wherein X and Y are as defined above, with an ester of anhydroecgonine (1) having the formula:

1

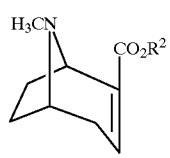

wherein $R^2$ is as defined above to obtain a compound (2) having the formula:

2

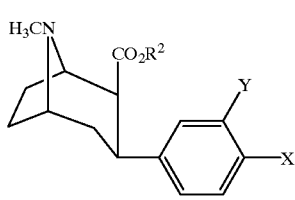

2) conversion of compound (2) into compound (3) having the formula:

3

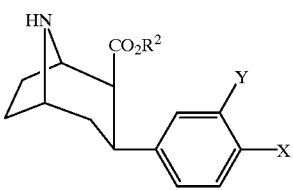

through reaction with trichloroethyl chloroformate and reduction with zinc and acetic acid, 3) conversion of compound 3 into compound (5) having the formula:

5

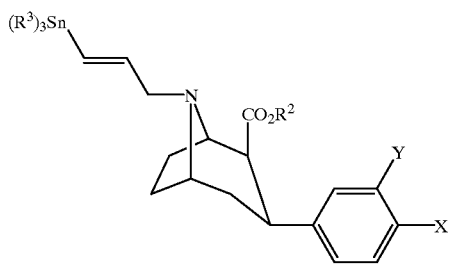

wherein $R^3$ is an alkyl group, and 4) reaction of compound (5) with the iodide of formula Na*I wherein *I is a radioactive isotope of iodine, in the presence of an oxidizing agent.

26. The process of claim 24, wherein in stage 3) compound (3) is converted directly into compound (5) through reaction with 3-chloro-1-trialkylstannyl-prop-1-ene.

27. The process of claim 25, wherein in stage 3) compound (3) is converted directly into compound 5 through reaction with 3-chloro-1-trialkylstannyl-prop-1-ene.

28. The process of claim 24, wherein in stage 3) firstly compound (3) is caused to react with 1-bromo-2-propyne to obtain the compound having the formula:

4

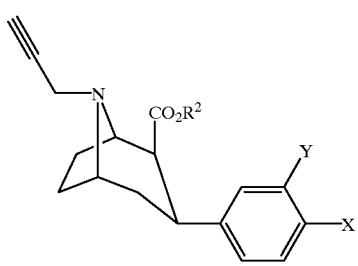

then compound (4) is caused to react with trialkylstannyl hydride to obtain compound (5).

29. The process of claim 25, wherein in stage 3) firstly compound (3) is caused to react with 1-bromo-2-propyne to obtain the compound having the formula:

4

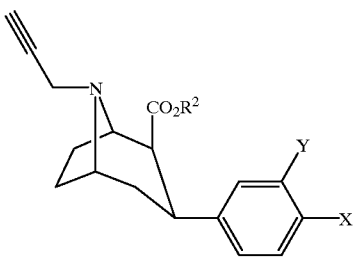

then compound (4) is caused to react with trialkylstannyl hydride to obtain compound (5).

30. A process for preparing a compound represented by the formula:

(I)

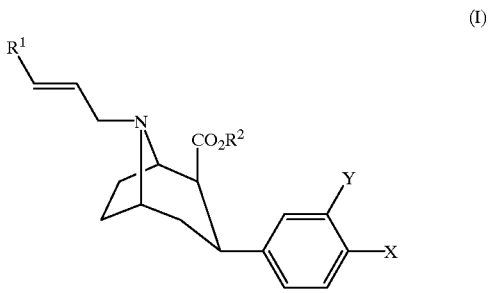

wherein $R^1$ represents $Sn(C_4H_9)_3$, $^{125}I$, $^{123}I$ or $^{131}I$, $R^2$ represents $CH_3$, X represents $CH_3$, and Y represents H, comprising:

1) reaction of an arylmagnesium bromide having the formula:

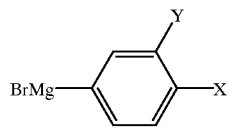

wherein X and Y are as defined above, with an ester of anhydroecgonine (1) having the formula:

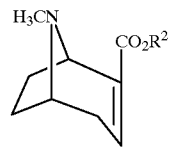

wherein $R^1$ is as defined above, to obtain a compound (2) having the formula:

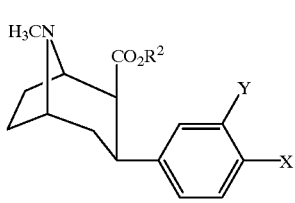

2) conversion of compound (2) into compound (3) having the formula:

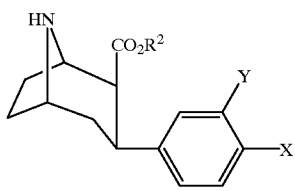

through reaction with trichloroethyl chloroformate and reduction with zinc and acetic acid, 3) conversion of compound (3) into compound (5) having the formula:

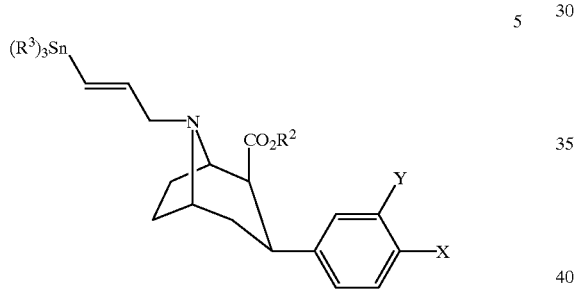

wherein $R^3$ is an alkyl group, and 4) reaction of compound (5) with iodine to obtain the compound of formula (1) as defined above.

31. A process for preparing a compound represented by the formula:

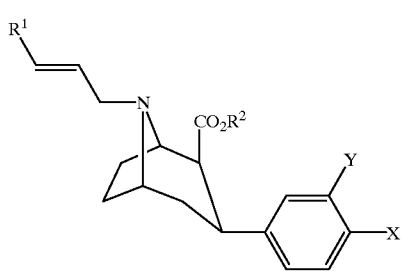

wherein $R^1$ represents $Sn(C_4H_9)_3$, $^{125}I$, $^{123}I$ or $^{131}I$, $R^2$ represents $CH_3$, X represents $CH_3$, and Y represents H, comprising:

1) reaction of an arylmagnesium bromide having the formula:

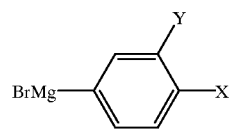

wherein X and Y are as defined above, with an ester of anhydroecgonine (1) having the formula:

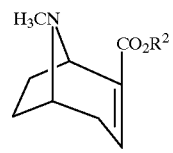

wherein $R^2$ is as defined above to obtain a compound (2) having the formula:

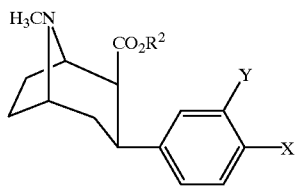

2) conversion of compound (2) into compound (3) having the formula:

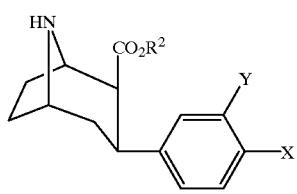

through reaction with trichloroethyl chloroformate and reduction with zinc and acetic acid, 3) conversion of compound 3 into compound (5) having the formula:

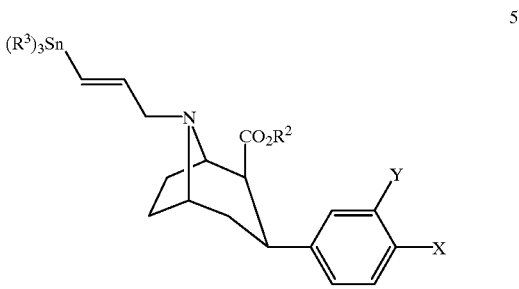

wherein $R^3$ is an alkyl group, and 4) reaction of compound (5) with the iodide of formula Na*I wherein *I is a radioactive isotope of iodine, in the presence of an oxidizing agent.

32. The process of claim 30, wherein in stage 3) compound (3) is converted directly into compound (5) through reaction with 3-chloro-1-trialkylstannyl-prop-1-ene.

33. The process of claim 31, wherein in stage 3) compound (3) is converted directly into compound 5 through reaction with 3-chloro-1-trialkylstannyl-prop-1-ene.

34. The process of claim 30, wherein in stage 3) firstly compound (3) is caused to react with 1-bromo-2-propyne to obtain the compound having the formula:

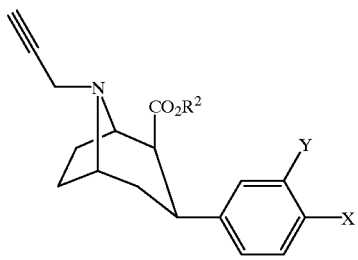

4 then compound (4) is caused to react with trialkylstannyl hydride to obtain compound (5).

35. The process of claim 31, wherein in stage 3) firstly compound (3) is caused to react with 1-bromo-2-propyne to obtain the compound having the formula:

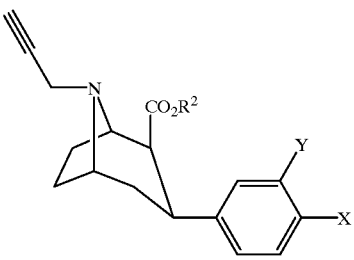

4 then compound (4) is caused to react with trialkylstannyl hydride to obtain compound (5).

36. The pharmaceutical composition of claim 35, for the visualization of dopamine transporters in the central nervous system.

* * * * *